United States Patent
Kim et al.

(10) Patent No.: US 10,130,300 B2
(45) Date of Patent: Nov. 20, 2018

(54) APPARATUS AND METHOD FOR ESTIMATING ANAEROBIC THRESHOLD

(71) Applicant: Samsung Electronics Co., Ltd., Suwon-si (KR)

(72) Inventors: Youn Ho Kim, Hwaseong-si (KR); Sang Kon Bae, Seongnam-si (KR); Kun Soo Shin, Seongnam-si (KR); Chang Mok Choi, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 965 days.

(21) Appl. No.: 14/082,686

(22) Filed: Nov. 18, 2013

(65) Prior Publication Data

US 2014/0141937 A1 May 22, 2014

(30) Foreign Application Priority Data

Nov. 16, 2012 (KR) .................. 10-2012-0130562

(51) Int. Cl.
| | |
|---|---|
| *A61B 5/00* | (2006.01) |
| *A61B 5/11* | (2006.01) |
| *A61B 5/0205* | (2006.01) |
| *A63B 24/00* | (2006.01) |
| *A61B 5/024* | (2006.01) |
| *A61B 5/22* | (2006.01) |

(52) U.S. Cl.
CPC .......... *A61B 5/4866* (2013.01); *A61B 5/0205* (2013.01); *A61B 5/02438* (2013.01); *A61B 5/1118* (2013.01); *A61B 5/222* (2013.01); *A63B 24/0062* (2013.01); *A61B 5/7282* (2013.01); *A61B 2503/10* (2013.01)

(58) Field of Classification Search
CPC combination set(s) only.
See application file for complete search history.

(56) References Cited

U.S. PATENT DOCUMENTS

| | | |
|---|---|---|
| 6,687,535 B2 | 2/2004 | Hautala et al. |
| 7,175,595 B1 | 2/2007 | Stegmann |
| 7,384,376 B2 | 6/2008 | Maschke |
| 7,674,226 B2 | 3/2010 | Nadeau |
| 7,764,990 B2 | 7/2010 | Martikka et al. |
| 7,993,268 B2 | 8/2011 | Nadeau |
| 8,052,580 B2 | 11/2011 | Saalasti et al. |

(Continued)

FOREIGN PATENT DOCUMENTS

| | | |
|---|---|---|
| CA | 2 355 849 | 7/2000 |
| CN | 1389176 A | 1/2003 |

(Continued)

OTHER PUBLICATIONS

Ignjatović, Aleksandar, Peter Hofmann, and Dragan Radovanović. "Non-invasive determination of the anaerobic threshold based on the heart rate deflection point." Facta universitatis-series: Physical Education and Sport 6.1 (2008): 1-10.*

Extended European Search Report dated Jan. 16, 2014 in counterpart European Patent Application No. 13193157.8. (5 pages in English).

X Li, "Heart Rate Control in Exercise Training", *Guizhou Sports Science and Technology*, Dec. 31, 1996, Issue 4, pp. 52-54.

(Continued)

*Primary Examiner* — Christian Jang
*Assistant Examiner* — Mitchell E Alter
(74) *Attorney, Agent, or Firm* — NSIP Law

(57) ABSTRACT

An apparatus for estimating an anaerobic threshold may include a heart rate detector configured to detect a heart rate from a signal sensed from a user, and an anaerobic threshold estimator configured to estimate an anaerobic threshold of the user based on a change in the detected heart rate.

5 Claims, 10 Drawing Sheets

(56) References Cited

U.S. PATENT DOCUMENTS

| | | | |
|---|---|---|---|
| 8,092,381 B2 | 1/2012 | Edwards | |
| 2006/0063980 A1* | 3/2006 | Hwang | A61B 5/222 600/300 |
| 2006/0079800 A1 | 4/2006 | Martikka et al. | |
| 2007/0060446 A1* | 3/2007 | Asukai | A63B 24/0021 482/8 |
| 2007/0275364 A1 | 11/2007 | Hassanein et al. | |
| 2008/0033311 A1* | 2/2008 | Sledge | A61B 5/024 600/509 |
| 2009/0024013 A1 | 1/2009 | Soller | |
| 2012/0029370 A1* | 2/2012 | Rocker | A61B 5/024 600/508 |
| 2012/0035021 A1 | 2/2012 | Saalasti et al. | |
| 2013/0053990 A1* | 2/2013 | Ackland | G06Q 30/02 700/91 |

FOREIGN PATENT DOCUMENTS

| | | |
|---|---|---|
| CN | 1932973 A | 3/2007 |
| CN | 1968293 A | 5/2007 |
| CN | 102387744 A | 3/2012 |
| JP | 2010-525076 A | 7/2010 |
| WO | WO 00/40151 A1 | 7/2000 |

OTHER PUBLICATIONS

H Zheng, "Attempt on Measurement of Anaerobic Threshold by 'Step Increasing Load Method'", *Sports Science Research*, Dec. 31, 1997, Issue. 3, pp. 17-18, 40.

Chinese Office Action dated Jan. 28, 2016 in counterpart Chinese Application No. 201310579063.2 (17 pages in Chinese with English translation).

\* cited by examiner

APPARATUS AND METHOD FOR ESTIMATING ANAEROBIC THRESHOLD

CROSS-REFERENCE TO RELATED APPLICATIONS

This application claims the benefit under 35 USC 119(a) of Korean Patent Application No. 10-2012-0130562 filed on Nov. 16, 2012, in the Korean Intellectual Property Office, the disclosure of which is incorporated herein by reference in its entirety for all purposes.

BACKGROUND

1. Field

The following description relates to an apparatus and method for estimating an anaerobic threshold based on a change in a condition of a user during exercise.

2. Description of Related Art

An exercise capacity test measures a level of physical exertion an individual is able to achieve before reaching a maximum heart rate. In some instances, an exercise capacity test may be hard on the individual's body. Also, it has been reported that results produced by an exercise capacity test may be overestimated.

As an alternative approach, an exercise capacity may be measured based on an anaerobic threshold. The anaerobic threshold is determined by testing a blood sample. However, drawing blood incurs displeasure, pain, and reluctance on the part of an individual. In addition, a blood testing device is expensive, and it is uncommon for an ordinary person to use one to determine an anaerobic threshold.

SUMMARY

In one general aspect, an apparatus for estimating an anaerobic threshold includes a heart rate detector configured to detect a heart rate from a signal sensed from a user; and an anaerobic threshold estimator configured to estimate an anaerobic threshold of the user based on a change in the heart rate.

The anaerobic threshold estimator may be further configured to estimate the anaerobic threshold based on a deflection point of the heart rate corresponding to the change in the heart rate.

The anaerobic threshold estimator may be further configured to estimate the anaerobic threshold based on a time it takes for the heart rate to reach a steady state at a predetermined exercise intensity of exercise being performed by the user, and the heart rate in the steady state.

In another general aspect, an apparatus for estimating an anaerobic threshold includes a kinetic energy calculator configured to calculate a kinetic energy of a physical motion sensed from a user; and an anaerobic threshold estimator configured to estimate an anaerobic threshold of the user based on a change in a heart rate of the user and the calculated kinetic energy.

The kinetic energy calculator may be further configured to monitor whether an exercise intensity of exercise being performed by the user is gradually increasing based on an amount of activity performed by the user measured based on the calculated kinetic energy.

The anaerobic threshold estimator may be further configured to estimate the anaerobic threshold based on a deflection point of the heart rate occurring while the exercise intensity is gradually increasing.

The anaerobic threshold estimator may be further configured to estimate the anaerobic threshold based on a deflection point of the heart rate corresponding to the change in the heart rate.

The anaerobic threshold estimator may be further configured to estimate the anaerobic threshold based on a time it takes for the heart rate to reach a steady state at a predetermined exercise intensity of exercise being performed by the user, and a heart rate in the steady state.

In another general aspect, an exercise guide apparatus includes an anaerobic threshold receiver configured to receive an anaerobic threshold of a user estimated based on a heart rate of the user from an anaerobic threshold estimating apparatus; and an exercise program provider configured to provide an exercise program to meet an exercise goal associated with personal information of the user based on the anaerobic threshold.

The exercise program provider may be further configured to adjust an exercise intensity of the exercise program based on the exercise goal associated with the personal information of the user and the anaerobic threshold.

In another general aspect, a method of estimating an anaerobic threshold includes detecting a heart rate from a signal sensed from a user; and estimating an anaerobic threshold of the user based on a change in the heart rate.

The estimating of the anaerobic threshold may include estimating the anaerobic threshold based on a deflection point of the heart rate corresponding to the change in the heart rate.

The estimating of the anaerobic threshold may include estimating the anaerobic threshold based on a time it takes for the heart rate to reach a steady state at a predetermined exercise intensity of exercise being performed by the user, and a heart rate in the steady state.

In another general aspect, a method of estimating an anaerobic threshold includes calculating a kinetic energy from a physical motion sensed from a user; and estimating an anaerobic threshold of the user based on a change in a heart rate of the user and the calculated kinetic energy.

The method may further include monitoring whether an exercise intensity of exercise being performed by the user is gradually increasing based on an amount of activity performed by the user measured based on the calculated amount of the kinetic energy.

The estimating of the anaerobic threshold may include estimating the anaerobic threshold based on a deflection point of the heart rate occurring while the exercise intensity is gradually increasing.

The estimating of the anaerobic threshold may include estimating the anaerobic threshold based on a deflection point of the heart rate corresponding to the change in the heart rate.

The estimating of the anaerobic threshold may include estimating the anaerobic threshold based on a time it takes for the heart rate to reach a steady state at a predetermined exercise intensity of exercise being performed by the user, and a heart rate in the steady state.

In another general aspect, an exercise guide method includes receiving an anaerobic threshold of a user estimated based on a heart rate of the user from an anaerobic threshold estimating apparatus; and providing an exercise program to meet an exercise goal associated with personal information of the user based on the anaerobic threshold.

The exercise guide method may further include adjusting an exercise intensity of the exercise program based on the exercise goal associated with the personal information of the user and the anaerobic threshold.

In another general aspect, an apparatus for estimating an anaerobic threshold includes a sensor configured to sense a signal from a user; and an estimator configured to detect whether an exercise intensity of exercise being performed by a user has a predetermined pattern based on the signal, and estimate an anaerobic threshold of the user in response to the exercise intensity having the predetermined pattern.

The predetermined pattern of exercise intensity may be a gradually increasing exercise intensity.

The apparatus may further include a second sensor configured to sense a second signal from the user; and the estimator may be further configured to estimate an anaerobic threshold of the user in response to the exercise intensity having the predetermined pattern based on the second signal.

The signal may be a signal indicative of a physical motion of the user; and the second signal may be a signal indicative of a heart rate of the user.

In another general aspect, an apparatus for estimating an anaerobic threshold includes a detector configured to detect a signal sensed from the user; and an estimator configured to estimate an anaerobic threshold of the user based on a change in the signal.

The estimator may be further configured to estimate the anaerobic threshold of the user based on a deflection point of the signal corresponding to the change in the signal.

The apparatus may further include a detector configured to detect a physical motion of the user; and the anaerobic threshold estimator may be further configured to estimate the anaerobic threshold based on the signal and the physical motion of the user.

The estimator may be further configured to estimate the anaerobic threshold based on the signal in response to the physical motion corresponding to a predetermined pattern of exercise intensity of exercise being performed by the user.

The predetermined pattern of exercise intensity may be a gradually increasing exercise intensity.

The estimator may be further configured to estimate the anaerobic threshold based on a time it takes for the signal to reach a steady state at a predetermined exercise intensity of exercise being performed by the user, and a value of the signal in the steady state.

Other features and aspects will be apparent from the following detailed description, the drawings, and the claims.

DETAILED DESCRIPTION

Figure 1:
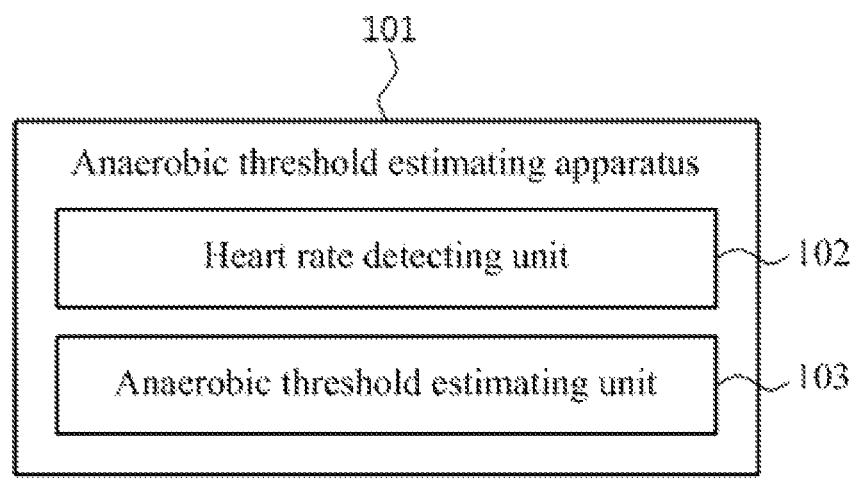
FIG. 1 is a block diagram illustrating an example of an apparatus for estimating an anaerobic threshold.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein and may be changed as will be apparent to one of ordinary skill in the art, with the exception of operations necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 is a block diagram illustrating an example of an apparatus 101 for estimating an anaerobic threshold. Referring to FIG. 1, the apparatus 101 for estimating an anaerobic threshold includes a heart rate detecting unit 102 and an anaerobic threshold estimating unit 103.

The heart rate detecting unit 102 may sense a potential signal from a user for use in detecting a change in a condition of the user during exercise. The heart rate detecting unit 102 may include a heart rate sensor, an electromyogram (EMG) sensor, or any other sensor capable of sensing the potential signal. The change in condition is a change in a physical condition of the user produced by exercise compared to a physical condition of the user at rest, for example, a change in a pulse, a change in a heart rate, or a change in any other physical condition. The potential signal may be a voltage signal. However, a current signal or any other type of signal may be sensed from the user using an appropriate sensor.

The heart rate detecting unit 102 may amplify the potential signal based on an intensity of the potential signal. The heart rate detecting unit 102 may filter the potential signal to extract a frequency band in which a heart rate may be detected, and detect the heart rate in the extracted frequency band. The heart rate detecting unit 102 may filter the potential signal sensed by a heart rate sensor, an EMG sensor, or other sensor to extract the frequency band in which the heart rate may be detected.

Also, the heart rate detecting unit 102 may monitor a change in the detected heart rate. By monitoring the change in the detected heart rate, the apparatus 101 for estimating an anaerobic threshold may calculate data for a change in a condition of the user during a course of exercise being performed by the user. Also, the apparatus 101 for estimating an anaerobic threshold may monitor a change in a heart rate to measure an anaerobic threshold of the user.

The anaerobic threshold estimating unit 103 may estimate an anaerobic threshold of the user based on the change in the heart rate. The anaerobic threshold estimating unit 103 may estimate the anaerobic threshold of the user based on a heart rate at a predetermined exercise intensity.

The anaerobic threshold estimating unit 103 may estimate the anaerobic threshold of the user based on a first heart rate deflection point rather than a maximum heart rate because an anaerobic threshold point may be approximated by the first heart rate deflection point. Accordingly, the anaerobic threshold estimating unit 103 may estimate the anaerobic threshold of the user without needing to know a maximum heart rate of the user. A further description of the anaerobic threshold estimation is provided below with reference to FIGS. 2 and 3.

As described in the foregoing, the apparatus 101 for estimating an anaerobic threshold may sense a potential signal from a user through a separate sensor, and estimate an anaerobic threshold of the user. The apparatus 101 for estimating an anaerobic threshold may operate with a minimum influence of an external environment by sensing the potential signal from the user through the sensor irrespective of a time and a location. For example, the apparatus 101 for estimating an anaerobic threshold may estimate the anaerobic threshold of the user by sensing the potential signal from the user irrespective of whether the user exercises indoors or outdoors.

Also, the apparatus 101 for estimating an anaerobic threshold may receive an input of an anaerobic threshold from the user if the user already knows his anaerobic threshold.

The apparatus 101 for estimating an anaerobic threshold may estimate the anaerobic threshold of the user through a treadmill, an exercise bike, or other exercise equipment capable of gradually increasing exercise intensity to the user.

Figure 2:
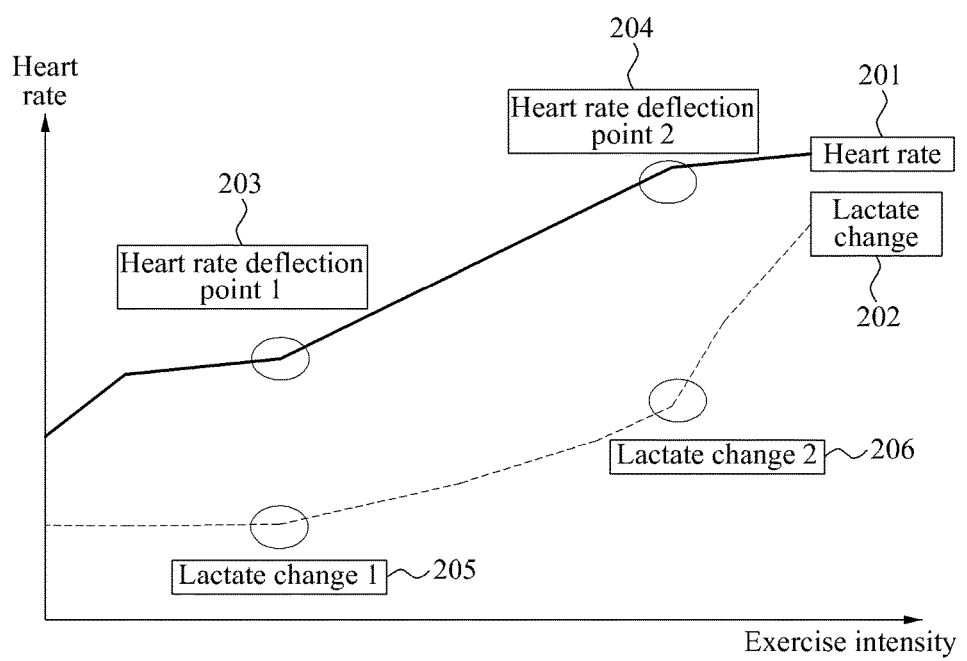
FIGS. 2 and 3 are graphs illustrating examples of a method of estimating an anaerobic threshold.
Figure 3:
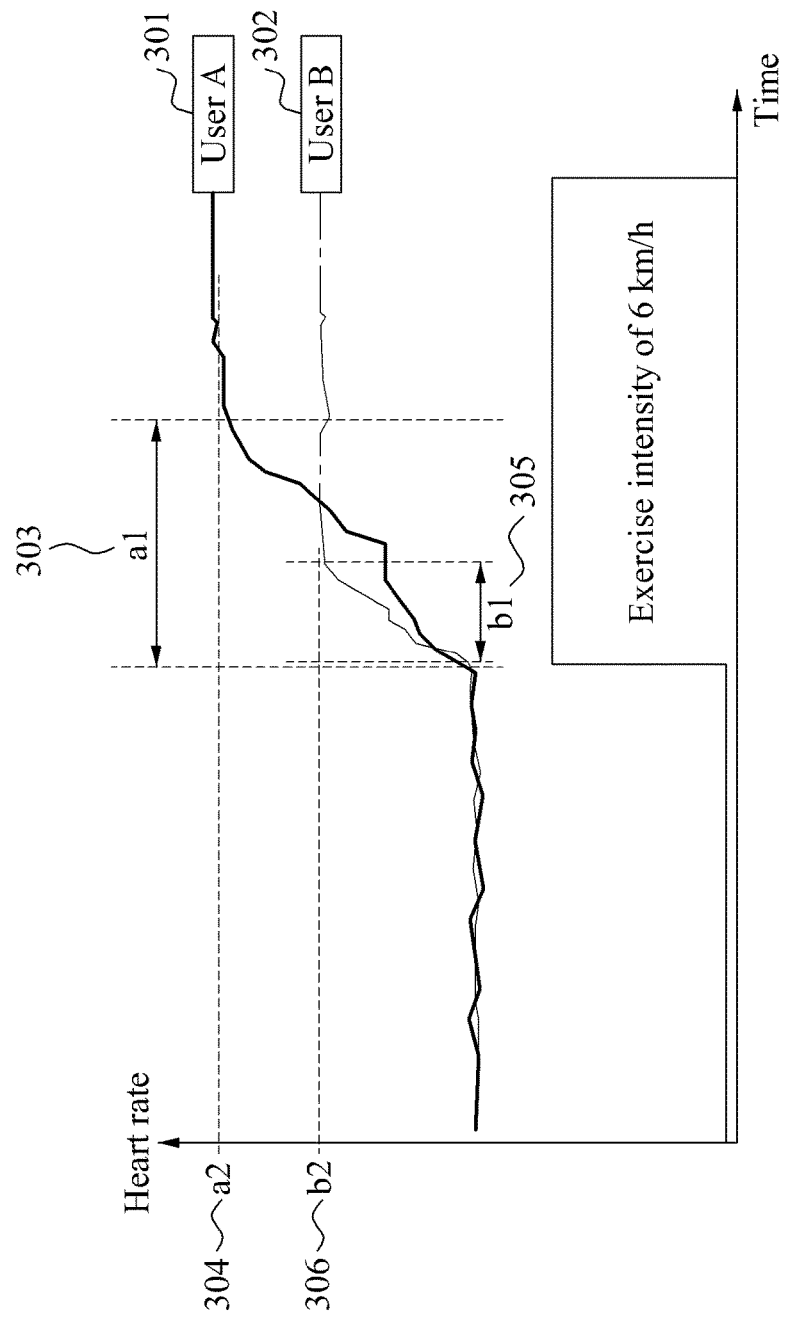

FIGS. 2 and 3 are graphs illustrating examples of a method of estimating an anaerobic threshold. Referring to FIG. 2, the anaerobic threshold estimating unit may estimate an anaerobic threshold based on a change in a heart rate 201 occurring during exercise having a gradually increasing exercise intensity. The anaerobic threshold estimating unit may estimate the anaerobic threshold based on a heart rate deflection point corresponding to the change in the heart rate 201. The anaerobic threshold estimating unit may extract the heart rate deflection point through differentiation of a regression change and differentiation of an inclination change based on data corresponding to the change in the heart rate 201. The anaerobic threshold estimating unit may extract the heart rate deflection point using various data extraction methods.

The reason for extracting the heart rate deflection point is that an anaerobic threshold point may be approximated by the heart rate deflection point. Accordingly, the anaerobic threshold estimating unit may estimate the anaerobic threshold by extracting the heart rate deflection point.

For example, the heart rate deflection point may include a first heart rate deflection point 203 and a second heart rate deflection point 204.

The first heart rate deflection point 203 is a first deflection point of the heart rate 201 changing during a course of exercise having a gradually increasing exercise intensity being performed by the user. The first heart rate deflection point 203 is a point at which a change in the heart rate 201 initially may occur after the user starts to exercise. The second heart rate deflection point 204 is a second deflection point of the heart rate 201 changing during the course of the exercise having a gradually increasing exercise intensity being performed by the user. The second heart rate deflection point 204 is a point at which the heart rate 201 reaches a maximum level due to continuous exercise performed by the user.

A lactate change 202 may occur in response to the exercise having a gradually increasing exercise intensity being performed by the user. The lactate change 202 may occur at points corresponding approximately to the first heart rate deflection point 203 and the second heart rate deflection point 204. A first lactate change 205 may occur at a point corresponding approximately to the first heart rate deflection point 203, and a second lactate change 206 may occur at a point corresponding approximately to the second heart rate deflection point 204.

Based on the correspondence between the deflection points of the heart rate 201 and the lactate change 202, the anaerobic threshold estimating unit may estimate an anaerobic threshold corresponding to the first lactate change 205 based on the first heart rate deflection point 203. This eliminates the need to detect the first lactate change 205 directly by testing a blood sample from the user.

Because the second heart rate deflection point 204 corresponds to a point at which the heart rate 201 reaches a maximum level during the exercise having a gradually increasing exercise intensity performed by the user, a user's body may be stressed before reaching the second heart rate deflection point 204. Accordingly, the anaerobic threshold estimating unit may estimate the anaerobic threshold based on the first heart rate deflection point 203 rather than the second heart rate deflection point 204 to minimize the stress on the user's body.

Referring to FIG. 3, the anaerobic threshold estimating unit may estimate an anaerobic threshold based on a predetermined exercise intensity. The predetermined exercise intensity may be an exercise intensity defined at a predetermined level for estimating the anaerobic threshold. The anaerobic threshold estimating unit may measure a change in a heart rate at the predetermined exercise intensity. The anaerobic threshold estimating unit may estimate an anaerobic threshold based a steady state attained by the heart rate being measured. The steady state is a state in which a physical response, for example, a heart rate, is remains constant while the user exercises. The anaerobic threshold estimating unit may estimate the anaerobic threshold based on a time it takes for a heart rate to reach a steady state, and the heart rate in the steady state.

For example, the anaerobic threshold estimating unit may measure a heart rate of a user A 301 and a heart rate of a user B 302 in response to a predetermined exercise intensity, for example, walking at 6 km/h. In FIG. 3, a1 303 and b1 305 denote a time it takes for the heart rate to reach a steady state, and a2 304 and b2 306 denote an average heart rate in the steady state.

The heart rate of the user A 301 reaches a steady state during a time a1 303, and the heart rate of the user B 302 reaches a steady state during a time b1 305. The time a1 303 is longer than the time b1 305.

As the anaerobic threshold increases, the time it takes for the heart rate to reach the steady state in response to a predetermined exercise intensity decreases as shown by the interval a1 303 and the interval b1 305, and the heart rate in the steady state decreases as shown in the heart rate a2 304 and the heart rate b2 306. That is, a higher anaerobic threshold may be characterized by a shorter time for the heart rate to reach a steady state and a lower heart rate in the steady state.

Accordingly, the user B 302 having the shorter time for the heart rate to reach the steady state and the lower heart rate in the steady state may be determined to have a higher anaerobic threshold than the user A 301. The user B 302 may be estimated to have a higher exercise capacity than the user A 301 based on the higher anaerobic threshold of the user B 302.

For example, the anaerobic threshold estimating unit may estimate the anaerobic threshold using Equation 1.

The anaerobic threshold=$A$*(the time it takes for the heart rate to reach a steady state, i.e. $a1$ or $b1$)+ $B$*(the average heart rate in the steady state, i.e. $a2$ or $b2$)+$C$ [Equation 1]

In Equation 1, A, B, C denote constant.

The anaerobic threshold estimating unit may estimate the anaerobic threshold based on personal information associated with the exercise performed by the user. The personal information may include, for example, a body mass index (BMI), an age, a gender, a rest period, and any other personal information. For example, the anaerobic threshold estimating unit may modify Equation 1 based on the BMI, the age, the gender, the rest period and so on.

Figure 4:
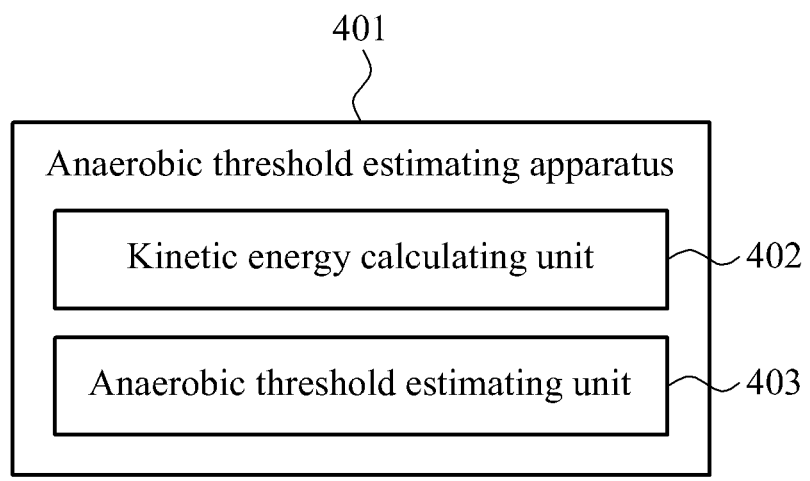
FIG. 4 is a block diagram illustrating another example of an apparatus for estimating an anaerobic threshold.

FIG. 4 is a block diagram illustrating another example of an apparatus 401 for estimating an anaerobic threshold. Referring to FIG. 4, the apparatus 401 for estimating an anaerobic threshold may include a kinetic energy calculating unit 402 and an anaerobic threshold estimating unit 403.

The kinetic energy calculating unit 402 may sense a physical motion of a user. The kinetic energy calculating unit 402 may sense the physical motion of the user from a sensor, for example, an acceleration sensor. The physical motion may include a motion vector magnitude (VM), a number of steps, or any other physical motion. The kinetic energy calculating unit 402 may calculate kinetic energy of the physical motion based on the sensed physical motion. The kinetic energy calculating unit 402 may calculate the kinetic energy by integrating the sensed physical motion.

The kinetic energy calculating unit 402 may measure an amount of activity performed by the user based on the calculated kinetic energy. The kinetic energy calculating unit 402 may monitor whether an exercise intensity is gradually increasing based on the measured amount of activity.

The anaerobic threshold estimating unit 403 may estimate an anaerobic threshold based on a heart rate deflection point and the amount of activity performed by the user. The estimating of the anaerobic threshold based on the amount of activity performed by the user is described in further detail below with reference to FIG. 5.

The anaerobic threshold estimating unit 403 may estimate the anaerobic threshold of the user based on a change in a heart rate. The anaerobic threshold estimating unit 403 may estimate the anaerobic threshold of the user based on a change in a heart rate at a predetermined exercise intensity.

The anaerobic threshold estimating unit 403 may estimate the anaerobic threshold of the user based on a first heart rate deflection point rather than a maximum heart rate because an anaerobic threshold point may be approximated by the first heart rate deflection point. Accordingly, the anaerobic threshold estimating unit 403 may estimate the anaerobic threshold of the user without needing to know a maximum heart rate of the user.

The anaerobic threshold estimating unit 403 may estimate the anaerobic threshold based on a time it takes for a heart rate to reach a steady state at a predetermined exercise intensity, and the heart rate in the steady state.

Accordingly, the apparatus 401 for estimating an anaerobic threshold may estimate the anaerobic threshold based on a heart rate of the user at rest, a heart rate based on an amount of activity performed by the user, and a heart rate at a predetermined exercise intensity.

Figure 5:
FIG. 5 is a graph illustrating another example of a method of estimating an anaerobic threshold.

FIG. 5 is a graph illustrating another example of a method of estimating an anaerobic threshold. Referring to FIG. 5, the anaerobic threshold estimating unit may estimate an anaerobic threshold based on a heart rate changing with a change in an amount of activity performed by a user. The amount of activity may increase rapidly when an exercise intensity changes due to a change in motion. For example, the amount of activity may increase rapidly when an exercise intensity changes from walking to running. Also, a heart rate may increase with a change in an amount of activity. However, a heart rate increasing rapidly with a change in an amount of activity may be different from a heart rate suitable for estimating an anaerobic threshold. Accordingly, the anaerobic threshold estimating unit may estimate an anaerobic threshold based on a heart rate deflection point of a heart rate gradually increasing with a gradual increase in an amount of activity produced by a gradual increase in an exercise intensity, rather than a heart rate increasing rapidly with a change in an amount of activity.

Accordingly, the anaerobic threshold estimating unit may estimate an anaerobic threshold based on a heart rate deflection point occurring during a gradual increase in an amount of activity.

Figure 6:
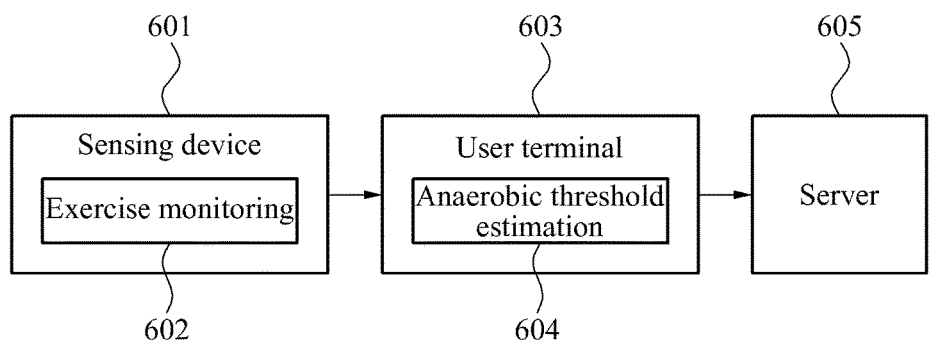
FIG. 6 is a schematic block diagram illustrating an example of a user terminal for estimating an anaerobic threshold.

FIG. 6 is a schematic block diagram illustrating an example of a user terminal for estimating an anaerobic threshold. Referring to FIG. 6, a sensing device 601 may perform exercise monitoring 602. The sensing device 601 may sense a potential signal from a user for use in detecting a change in a condition of the user during exercise. The sensing device 601 may transmit the sensed potential signal of the user to a user terminal 603 capable of transmitting and receiving data. The sensing device 601 may interoperate with or be connected to the user terminal 603 via a wireless communication.

The user terminal 603 may perform anaerobic threshold estimation 604. The user terminal 603 may estimate an anaerobic threshold of the user based on the sensed potential signal. The user terminal 603 may estimate the anaerobic threshold based on data corresponding to a change in a heart rate of the user. In particular, the user terminal 603 may estimate the anaerobic threshold based on a heart rate deflection point corresponding to the change in the heart rate of the user. The user terminal 603 may set an exercise goal of the user based on the estimated anaerobic threshold. The user terminal 603 may provide the user with the exercise goal of the user.

The user terminal 603 may may interoperate with a server 605. The server 605 may receive data associated with the anaerobic threshold of the user or the exercise goal of the user from the user terminal 603. The server 603 may share the received data with users of a social network.

Accordingly, the sensing device 601 may sense a potential signal from a user, and may transmit the sensed potential signal to the user terminal 603. The user terminal 603 may estimate an anaerobic threshold of the user based on the received potential signal.

Figure 7:
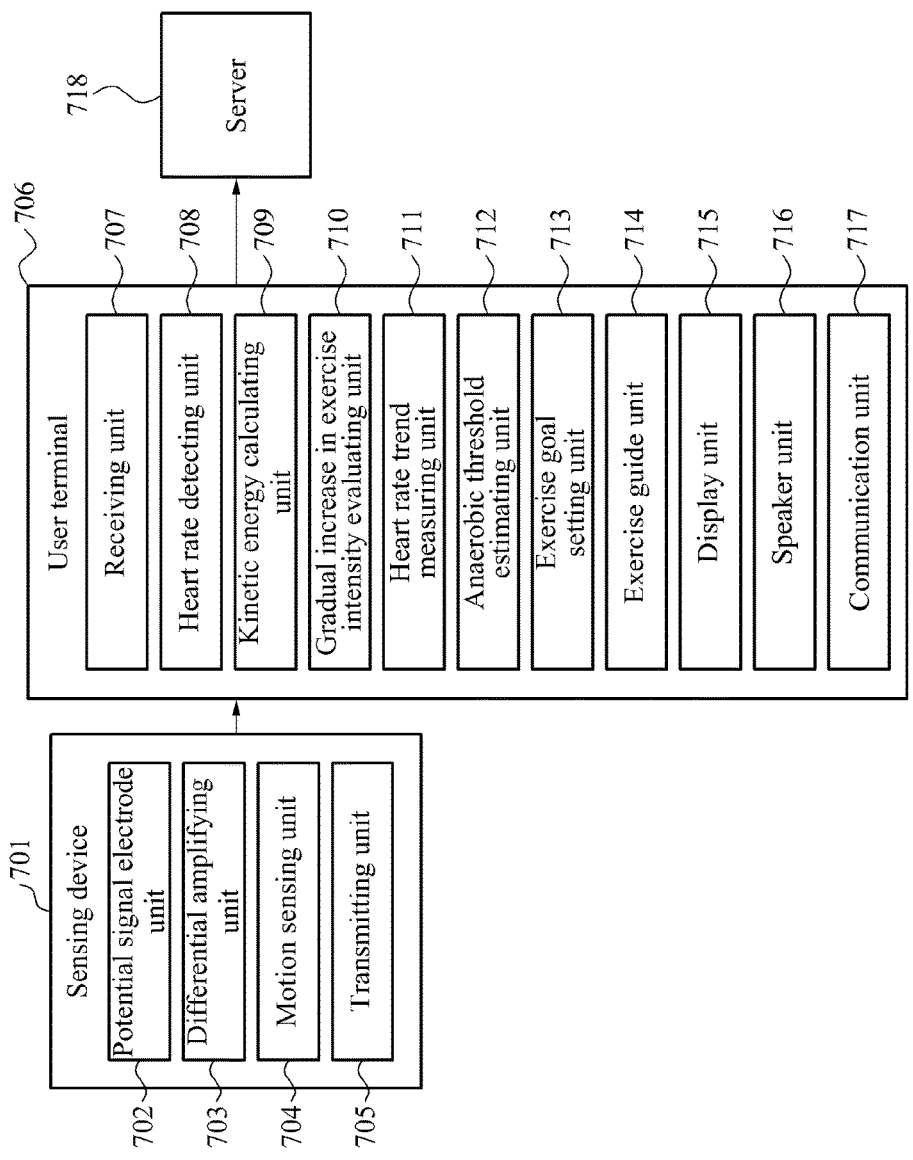
FIG. 7 is a detailed block diagram illustrating a detailed example of the user terminal of FIG. 6 for estimating an anaerobic threshold.

FIG. 7 is a detailed block diagram illustrating a detailed example of the user terminal of FIG. 6 for estimating an anaerobic threshold. Referring to FIG. 7, a sensing device 701 may include a potential signal electrode unit 702, a differential amplifying unit 703, a motion sensing unit 704, and a transmitting unit 705.

The potential signal electrode unit 702 may sense a potential signal from a user for use in detecting a change in a condition of the user during exercise.

The differential amplifying unit 703 may differentially amplify the potential signal of the user based on an intensity of the potential signal. The differential amplifying unit 703 may amplify the potential signal of the user based on the intensity of the potential signal to extract the potential signal.

The motion sensing unit 704 may sense a physical motion of the user. The motion sensing unit 704 may sense the physical motion from a sensor, for example, an acceleration sensor, an angular velocity sensor, a motion sensor, or any other sensor capable of sensing physical motion. The motion sensing unit 704 may sense the physical motion of the user for use in detecting a gradually increasing exercise intensity of exercise performed by the user when the user is not using a treadmill or an exercise bike capable of providing a gradually increasing exercise intensity.

The transmitting unit 705 may transmit the sensed potential signal and the sensed physical motion of the user to a user terminal 706.

The user terminal 706 may include a receiving unit 707, a heart rate detecting unit 708, a kinetic energy calculating unit 709, a gradual increase in exercise intensity evaluating unit 710, a heart rate trend measuring unit 711, an anaerobic threshold estimating unit 712, an exercise goal setting unit 713, an exercise guide unit 714, a display unit 715, and a communication unit 717. The user terminal 706 may further include a speaker unit 716 depending on an environment in which the user terminal 706 is to be used.

The receiving unit 707 may receive the sensed potential signal and the sensed physical motion of the user from the sensing device 701.

The heart rate detecting unit 708 may filter the sensed potential signal to extract a frequency band in which a heart rate may be detected, and may detect the heart rate in the extracted frequency band. The heart rate detecting unit 708 may detect the heart rate from a potential signal sensed from any of various types of sensors capable of measuring a physical change of the user, such as a heart rate sensor, an EMG sensor, or other sensor.

The kinetic energy calculating unit 709 may calculate a kinetic energy based on the physical motion sensed by the motion sensing unit 704. The physical motion may include a motion VM, a number of steps, or any other physical motion. The motion VM may be determined based on an acceleration value from an acceleration sensor. The kinetic energy calculating unit 709 may measure an amount of activity performed by the user based on the calculated kinetic energy. The kinetic energy calculating unit 709 may calculate the kinetic energy by performing integrating the sensed physical motion.

The gradual increase in exercise intensity evaluating unit 710 may monitor an exercise intensity based on the measured amount of activity. The gradual increase in exercise intensity evaluating unit 710 may monitor whether an exercise intensity of exercise being performed by the user is gradually increasing. If the exercise intensity is gradually increasing, an anaerobic threshold may be estimated. If the exercise intensity is not gradually increasing, for example, if the exercise intensity is not changing, or is decreasing, or is randomly fluctuating, or is abruptly or rapidly changing, an anaerobic intensity may not be estimated. By monitoring an exercise intensity based on the measured amount of activity, the gradual increase in exercise intensity evaluating unit 710 may distinguish between different amounts of activity, for example, when the user walks and when the user runs. The gradual increase in exercise intensity evaluating unit 710 may monitor the exercise intensity based on the motion VM. For example, The gradual increase in exercise intensity evaluating unit 710 may determine that the exercise intensity is gradually increasing when the motion VM is gradually increasing.

The gradual increase in exercise intensity evaluating unit 710 may estimate an amount of activity based on the heart rate detected by the heart rate detecting unit 708, and may monitor an exercise intensity based on the estimated amount of activity. The amount of activity and the heart rate increase in proportion to an exercise intensity of exercise being performed by the user.

The heart rate trend measuring unit 711 may monitor a change in a heart rate based on the sensed potential signal or the sensed physical motion signal. By monitoring the change in the heart rate, the heart rate trend measuring unit 711 may calculate data for a change in a condition of the user while the user is performing exercise.

The anaerobic threshold estimating unit 712 may estimate an anaerobic threshold based on data associated with the change in the heart rate if the gradual increase in exercise intensity evaluating unit 710 determines that an exercise intensity is gradually increasing. The anaerobic threshold estimating unit 712 may estimate the anaerobic threshold based on a heart rate deflection point. The anaerobic threshold estimating unit 712 may extract the heart rate deflection point using differentiation of a regression change and differentiation of an inclination change based on data corresponding to the change in the heart rate. The anaerobic threshold estimating unit 712 may estimate the anaerobic threshold based on a first heart rate deflection point based on a characteristic that a heart rate deflection point approximates an anaerobic threshold point. The anaerobic threshold estimating unit 712 may minimize a stress on a body of the user by estimating the anaerobic threshold based on a heart rate at a low exercise intensity corresponding to the first heart rate deflection point.

Alternatively, the anaerobic threshold estimating unit 712 may estimate the anaerobic threshold based on a predetermined exercise intensity. The anaerobic threshold estimating unit 712 may measure a change in a heart rate at the predetermined exercise intensity. The anaerobic threshold estimating unit 712 may estimate the anaerobic threshold based on a time it takes for the heart rate to reach a steady state at the predetermined exercise intensity, and the heart rate in the steady state.

The anaerobic threshold estimating unit 712 may estimate the anaerobic threshold based on a characteristic that as an anaerobic threshold increases, the time it takes for a heart rate to reach a steady state at a predetermined exercise intensity decreases, and the heart rate in the steady state decreases.

The exercise goal setting unit 713 may set an exercise goal of the user based on the estimated anaerobic threshold. The exercise goal setting unit 713 may set the exercise goal corresponding to a purpose of the exercise based on the anaerobic threshold and the heart rate of the user.

The exercise guide unit 714 may provide the user with a guide to an exercise program suitable for the user based on the exercise goal that has been set. The exercise guide unit 714 may provide the user with a guide to an individualized exercise program to meet the purpose of exercise, for example, weight loss, cardiovascular endurance improvement, or any other purpose of exercise.

The display unit 715 may display the exercise program on the user terminal 706. The display unit 715 may display various user information, for example, an exercise goal, exercise state data, or any other user information. The display unit 715 may enable the user to adjust items to be displayed to enable the display unit 715 to display personalized user information.

The speaker unit 716 may provide exercise state data of the user through a speaker. The speaker unit 716 may provide the exercise data of the user through the speaker, for example, a number of may set for exercise being performed, a heart rate, an anaerobic threshold, or any other exercise data.

The communication unit 717 may interoperate with a server 718. The server 718 may interoperate with the user terminal 706. The server 718 may receive data of the user, for example, an anaerobic threshold, from the user terminal 706, and may stored the data. The server 718 may provide the stored data to the user terminal 706 in response to a request from the user terminal 706. The server 718 may share the stored data with users of a social network, and may perform a trend analysis on the stored data.

Figure 8:
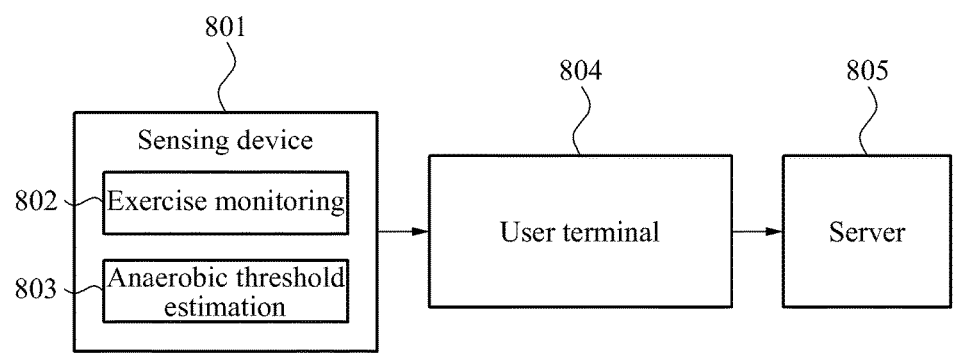
FIG. 8 is a schematic block diagram illustrating another example of a user terminal for estimating an anaerobic threshold.

FIG. 8 is a schematic block diagram illustrating another example of a user terminal for estimating an anaerobic threshold. Referring to FIG. 8, a sensing device 801 may perform exercise monitoring 802 and anaerobic threshold estimation 803. The sensing device 801 may sense a potential signal from a user, and may estimate an anaerobic threshold based on the potential signal of the user. The sensing device 801 may sense a potential signal or a physical motion from a user. The sensing device 801 may estimate an anaerobic threshold based on the potential signal or the physical motion of the user.

The sensing device 801 may differentially amplify the potential signal of the user based on an intensity of the potential signal.

The sensing device 801 may estimate an anaerobic threshold of the user based on the potential signal or the physical motion of the user. The sensing device 801 may monitor the potential signal and the physical motion of the user. The sensing device 801 may monitor the potential signal and the physical motion of the user based on a change in a heart rate of the user, or an amount of activity performed by the user measured based on a kinetic energy calculated from the physical motion of the user. The sensing device 801 may estimate an anaerobic threshold based on a time it takes for a heart rate to reach a steady state at a predetermined exercise intensity, and the heart rate in the steady state.

The sensing device 801 may set an exercise goal suitable for the user based on the anaerobic threshold and the heart rate, and may provide the user a guide to an exercise program corresponding to the exercise goal. The sensing device 801 may interoperate with or connects to a user terminal 804 via a wireless communication.

The user terminal 804 may receive a signal related to the anaerobic threshold and the heart rate of the user, and may provide the received signal to the user.

The user terminal 804 may interoperate with a server 805. The server 805 may receive data of the user, for example, an anaerobic threshold, from the user terminal 804, and may store the data. The server 805 may share the stored data with users of a social network, and may conduct a trend analysis on the stored data. The server 805 may provide the stored data to the user terminal 804 in response to a request from the user terminal 804.

Figure 9:
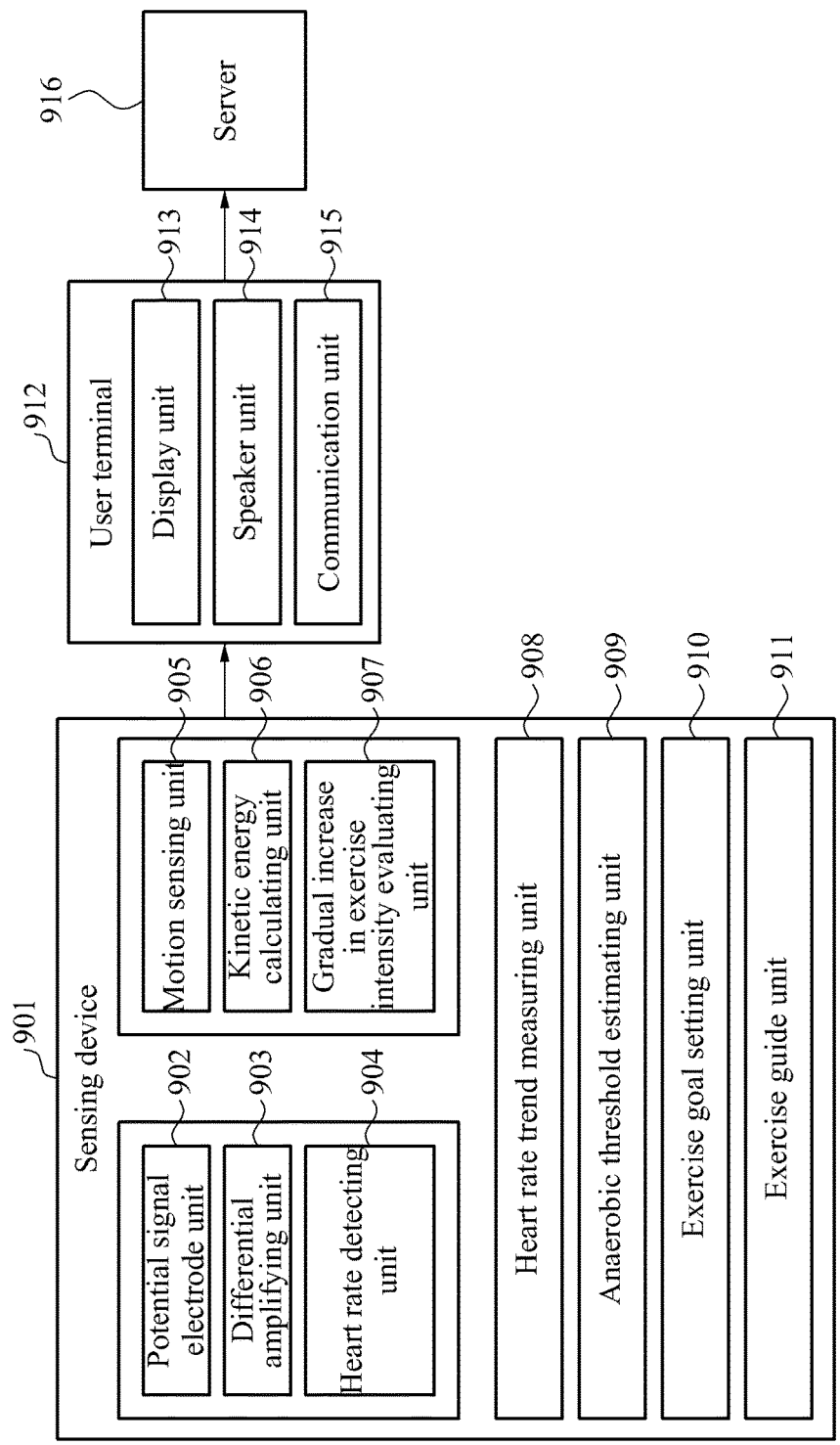
FIG. 9 is a detailed block diagram illustrating a detailed example of the user terminal of FIG. 8 for estimating an anaerobic threshold.

FIG. 9 is a detailed block diagram illustrating a detailed example of the user terminal of FIG. 8 for estimating an anaerobic threshold. Referring to FIG. 9, a sensing device 901 may include a potential signal electrode unit 902, a differential amplifying unit 903, a heart rate detecting unit 904, a motion sensing unit 905, a kinetic energy calculating unit 906, a gradual increase in exercise intensity evaluating unit 907, a heart rate trend measuring unit 908, an anaerobic threshold estimating unit 909, an exercise goal setting unit 910, and an exercise guide unit 911.

The potential signal electrode unit 902 may sense a potential signal from a user.

The differential amplifying unit 903 may differentially amplify the potential signal of the user based on an intensity of the potential signal.

The heart rate detecting unit 904 may filter the sensed potential signal to extract a frequency band in which a heart rate may be detected, and may detect a heart rate in the extracted frequency band. The heart rate detecting unit 904 may detect the heart rate from a potential signal sensed from any of various types of sensors capable of measuring a physical change of the user, such as a heart rate sensor, an EMG sensor, or other sensor.

The motion sensing unit 905 may sense a physical motion of the user from a sensor, for example, an acceleration sensor, an angular velocity sensor, a motion sensor, or any other sensor capable of sensing physical motion.

The kinetic energy calculating unit 906 may calculate a kinetic energy based on the sensed physical motion, and may measure an amount of activity based on the calculated kinetic energy. The kinetic energy calculating unit 906 may calculate the kinetic energy by integrating the physical motion.

The gradual increase in exercise intensity evaluating unit 907 may monitor an exercise intensity based on the amount of activity measured by the kinetic energy calculating unit 906. The gradual increase in exercise intensity evaluating unit 907 may monitor whether an exercise intensity is gradually increasing to determine whether an anaerobic threshold is to be estimated.

The heart rate trend measuring unit 908 may monitor a change in a heart rate based on the sensed potential signal and the sensed physical motion. The heart rate trend measuring unit 908 may calculate data for a change in a condition of the user while the user is performing exercise by monitoring the change in the heart rate.

The anaerobic threshold estimating unit 909 may estimate an anaerobic threshold based on data associated with the change in the heart rate. The anaerobic threshold estimating unit 909 may estimate the anaerobic threshold based on a heart rate deflection point.

The exercise goal setting unit 910 may set an exercise goal of the user corresponding to a purpose of exercise based on the anaerobic threshold and the heart rate of the user.

The exercise guide unit 911 may provide the user with a guide to an individualized exercise program to meet the purpose of exercise, for example, weight loss, cardiovascular endurance improvement, or any other purpose of exercise.

A user terminal 912 may include a display unit 913 and a communication unit 915. The user terminal 912 may further include a speaker unit 914 depending on an environment in which the user terminal 912 is to be used.

The display unit 913 displays the exercise program on the user terminal 912. The display unit 913 may display various user information, for example, an exercise goal, exercise state data, and or any other user information. The display unit 913 may enable the user to adjust items to be displayed to enable the display unit 913 to display personalized user information.

The speaker unit 914 may provide exercise state data of the user through a speaker. The speaker unit 914 may provide the exercise data of the user through the speaker, for example, a number of may set for exercise currently being performed, a heart rate, an anaerobic threshold, or any other exercise data.

The communication unit 915 may interoperate with a server 916. The server 916 may interoperate with the user terminal 912. The server 916 may receive data of the user, for example, an anaerobic threshold, from the user terminal 912, and store the data. The server 916 may share the stored data with users of a social network, and may conduct a trend analysis on the stored data. The server 916 may provide the stored data to the user terminal 912 in response to a request from the user terminal 912.

The server 605 of FIG. 6, the server 718 of FIG. 7, the server 805 of FIG. 8, and the server 916 of FIG. 9 may be included or excluded.

Figure 10:
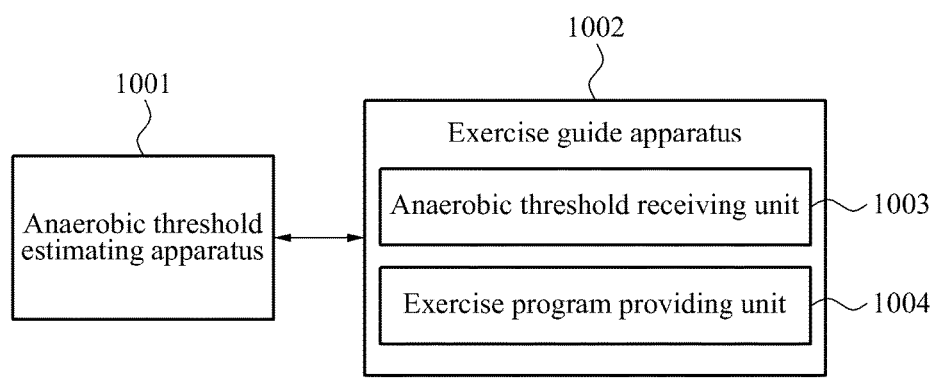
FIG. 10 is a block diagram illustrating an example of an exercise guide apparatus.

FIG. 10 is a block diagram illustrating an example of an exercise guide apparatus 1002. Referring to FIG. 10, the exercise guide apparatus 1002 may include an anaerobic threshold receiving unit 1003 and an exercise program providing unit 1004.

The anaerobic threshold receiving unit 1003 may receive an anaerobic threshold of a user estimated based on a heart rate of the user from the anaerobic threshold estimating apparatus 1001.

The exercise program providing unit 1004 may provide the user with a suitable exercise program for a purpose of exercise associated with personal information based on the anaerobic threshold. The personal information may include a weight, a height, a human body fat, an exercise intensity, or any other personal information.

The exercise program providing unit 1004 may provide the exercise program by adjusting an exercise intensity based on the personal information associated with the purpose of exercise. The exercise program providing unit 1004 may estimate an exercise capacity of the user based on the anaerobic threshold. The exercise capacity is a level of physical exertion that the user is able to achieve during exercise. The exercise capacity may be a maximum exercise intensity of the user.

For a user determined to have a high exercise capacity based on the anaerobic threshold, the exercise program providing unit 1004 may provide an exercise program having an exercise intensity exceeding the anaerobic threshold designed to improve the exercise capacity and the cardiovascular endurance of the user. For a user determined to have a low exercise capacity based on the anaerobic threshold, the exercise program providing unit 1004 may provide an exercise program having an exercise intensity near the anaerobic threshold but not exceeding the anaerobic threshold designed to maintain a level of fitness of the user or to burn fat. The exercise program providing unit 1004 may provide a user with an individualized exercise program to meet an exercise capacity of a user based on an anaerobic threshold. The exercise guide apparatus 1002 may enable a user to maximize an exercise effect within a given time period by providing the user with an optimal exercise program for an exercise capacity of the user.

The apparatus 101 for estimating an anaerobic threshold, the heart rate detecting unit 102, and the anaerobic threshold estimating unit 103 illustrated in FIG. 1; the apparatus 401 for estimating an anaerobic threshold, the kinetic energy calculating unit 402, and the anaerobic threshold estimating unit 403 illustrated in FIG. 4; the sensing device 601, the user terminal 603, and the server 605 illustrated in FIG. 6; the sensing device 701, the potential signal electrode unit 702, the differential amplifying unit 703, the motion sensing unit 704, the transmitting unit 705; the user terminal 706, the receiving unit 707, the heart rate detecting unit 708, the kinetic energy calculating unit 709, the gradual increase in exercise intensity evaluating unit 710, the heart rate trend measuring unit 711, the anaerobic threshold estimating unit 712, the exercise goal setting unit 713, the exercise guide unit 714, the display unit 715, the speaker unit 716, the communication unit 717, and the server 718 illustrated in FIG. 7; the sensing device 801, the user terminal 804, and the server 805 illustrated in FIG. 8; the sensing device 901, the potential signal electrode unit 902, the differential amplifying unit 903, the heart rate detecting unit 904, the motion sensing unit 905, the kinetic energy calculating unit 906, the gradual increase in exercise intensity evaluating unit 907, the heart rate trend measuring unit 908, the anaerobic threshold estimating unit 909, the exercise goal setting unit 910, the exercise guide unit 911, the user terminal 912, the display unit 913, the speaker unit 914, the communication unit 915, and the server 916 illustrated in FIG. 9; and the anaerobic threshold estimating apparatus 1001 and the exercise guide apparatus 1002 illustrated in FIG. 10 that perform the various operations illustrated in FIGS. 2, 3, and 5 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for estimating an anaerobic threshold, the apparatus comprising:
    a heart rate detector configured to detect a heart rate from a signal sensed from a user;
    an anaerobic threshold estimator configured to estimate an anaerobic threshold of the user by using a correlation in which there is an inverse relationship between the anaerobic threshold and a time for the detected heart rate to reach steady state at a constant exercise intensity, and an inverse relationship between the anaerobic threshold and the detected heart rate in the steady state at the constant exercise intensity; and
    a displayer configured to display content based on the estimated anaerobic threshold.

2. The apparatus of claim 1, wherein the anaerobic threshold estimator is further configured to estimate the anaerobic threshold based on a deflection point of the detected heart rate corresponding to a change in the detected heart rate.

3. The apparatus of claim 2, wherein the deflection point comprises a first deflection point at which the change in the detected heart rate initially occurs after a time at which the user starts performing exercise, and a second deflection point at which the detected heart rate reaches a maximum level due to continuous exercise performed by the user after the time at which the user starts performing the exercise.

4. The apparatus of claim 1, wherein the correlation is $$H=A*T+B*R+C,$$

wherein H is the anaerobic threshold, A is a first constant, T is the time for the detected heart rate to reach the steady state, B is a second constant, R is an average of the detected heart rate in the steady state, and C is a third constant.

5. The apparatus of claim 1, wherein the correlation is modified based on any one or any combination of any two or more of a body mass index of the user, an age of the user, a gender of the user, and a rest period.

* * * * *